(12) United States Patent
Guttuso, Jr.

(10) Patent No.: US 7,288,525 B2
(45) Date of Patent: Oct. 30, 2007

(54) METHOD FOR LOWERING SERUM HOMOCYSTEINE

(75) Inventor: Thomas Guttuso, Jr., Snyder, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/321,130

(22) Filed: Dec. 28, 2005

(65) Prior Publication Data

US 2006/0252699 A1    Nov. 9, 2006

Related U.S. Application Data

(60) Provisional application No. 60/639,846, filed on Dec. 28, 2004.

(51) Int. Cl.
*A61K 38/00*    (2006.01)

(52) U.S. Cl. .......................... 514/18; 514/19; 514/557

(58) Field of Classification Search .................. 514/18, 514/19, 557
See application file for complete search history.

(56) References Cited

U.S. PATENT DOCUMENTS

| | | | | |
|---|---|---|---|---|
| 6,048,846 A | * | 4/2000 | Cochran | 514/168 |
| 6,361,800 B1 | * | 3/2002 | Cooper et al. | 424/630 |
| 6,417,232 B1 | * | 7/2002 | Berge | 514/546 |

* cited by examiner

*Primary Examiner*—David Lukton
*Assistant Examiner*—Hemant Khanna
(74) *Attorney, Agent, or Firm*—Hodgson Russ LLP

(57) ABSTRACT

The present invention provides a method for reducing the amount of homocysteine in the blood of an individual. The method comprises administering to the individual a composition comprising a homocysteine lowering agent in an amount effective to lower the amount of homocysteine in the blood of the individual. The homocysteine lowering agent is selected from A dipeptides consisting of isoleucine, leucine, valine, or glycine and combinations thereof; tripeptides consisting of isoleucine, leucine, valine, or glycine and combinations thereof; alpha-ketobutyrate; propionyl A CoA, and combinations thereof.

9 Claims, No Drawings

METHOD FOR LOWERING SERUM HOMOCYSTEINE

This application claims priority to U.S. patent application Ser. No. 60/639,846, filed Dec. 28, 2004, the disclosure of which is incorporated herein by reference.

This work was supported by Grant Numbers AT001709 from the National Institutes of Health. The Government has certain rights in the invention.

FIELD OF THE INVENTION

The present invention relates generally to methods for reducing homocysteine levels in an individual by administering a composition comprising a homocysteine lowering agent.

BACKGROUND OF THE INVENTION

Elevated serum homocysteine has been identified in multiple epidemiologic studies to be an independent risk factor for cardiovascular disease, stroke, depression, osteoporosis and dementia. The only known method to reduce homocysteine is through vitamin supplementation with folate, B12, and B6. Of these three vitamins, folate supplementation leads to the greatest homocysteine reduction with only slight additional benefit with B12 and B6 supplementation. In the U.S., federally-mandated folate supplementation of the food supply has been in effect since 1998, which has led to lower homocysteine levels in U.S. cohort studies. Therefore, one would expect to find homocysteine levels less responsive to vitamin supplementation in the U.S. population since the food supply is already supplemented with folate.

In a multi-centered clinical trial conducted in Switzerland and the U.S., 553 patients with known cardiovascular disease randomized to vitamin therapy of folate, B12, and B6 showed about a 30% reduction in homocysteine levels compared with subjects randomized to placebo. The vitamin therapy group also showed improved cardiovascular outcomes. However, there is an ongoing need for a method to reduce homocysteine levels in individuals.

SUMMARY OF THE INVENTION

The present invention provides a method for reducing the amount of homocysteine in the blood of an individual. The method comprises administering to the individual a composition comprising a homocysteine lowering agent in an amount effective to lower the amount of homocysteine in the blood of the individual.

In one embodiment, the homocysteine lowering agent is a leucine, isoleucine or valine, also referred to herein as "branched chain amino acids." A preferred amino acid is L-isoleucine.

In another embodiment, the homocysteine lowering agent is a mixture of branched chain amino acids.

In another embodiment, the homocysteine lowering agent is a dipeptide or tripeptide consisting of branched chain amino acids.

In additional embodiments, the homocysteine lowering agent can be selected from odd-chain fatty acids, propionyl CoA, biotin and alpha-ketobutyrate.

The composition comprising the homocysteine lowering agent can be administered to the individual by a variety of known techniques. In a preferred embodiment, the composition is administered orally.

DETAILED DESCRIPTION OF THE INVENTION

The present invention provides a method for reducing the amount of homocysteine in the blood of an individual. The method comprises administering to the individual a composition comprising a homocysteine lowering agent in an amount effective to lower the amount of homocysteine in the blood of the individual.

In one embodiment, the homocysteine lowering agent is a branched chain amino acid or a combination of branched chain amino acids. It is preferred to use a the L-form of the branched chain amino acids. A preferred amino acid is L-isoleucine. Each of the branched chain amino acids is commercially available, as are combinations thereof.

The branched chain amino acids may be administered by any method, such as intradermal, intramuscular, intraperitoneal, intravenous, subcutaneous, intranasal, transdermal and oral routes. A preferred route of administration is oral administration.

In the present invention, a preferred dosage is 3-5 grams of a branched chain amino acid or 3-5 grams of combinations thereof. A preferred regimen is 3-5 grams of L-isoleucine taken orally, divided into two doses per day. A preferred treatment period is at least ten days.

Examples of oral dosage forms include both solid and liquid dosage forms, specifically capsules, tablets, dietary supplements, powders, solutions, syrups, elixirs and the like, including timed release capsules and tablets. Further, pharmaceutically acceptable carriers, excipients and diluents can be used and include those which are well known in the art. Examples of such carriers, diluents and excipients include starch, sugars, talc and the like. Other additives well known in the art may also be included in compositions of the present invention. Examples of such additives include wetting agents, emulsifying agents, and sweetening agents.

In one embodiment, the homocysteine lowering agent is a dipeptide or tripeptide consisting of branched chain amino acids. In this regard, the dipeptide or tripeptide may consist of a single type of branched chain amino acid or any combination of branched chain amino acids. Without intending to be bound by any particular theory, it is considered that dipeptides or tripeptides have better absorption and therefore would permit lower dosages than single amino acid formulations. (See, for example, Nielsen, et al. (2003) Curr Drug Targets, Vol. 4(5): 373-88; Hu, et al. (1989). Pharm Res Vol. 6 (1): 66-70.). Dipeptides or tripeptides can be prepared according to conventional techniques and can be administered to an individual in the same manner as single amino acids.

In another embodiment, branched chain amino acids can be provided in a dipeptide or tripeptide pro-drug. In this regard, to formulate the pro-drug, glycine can be used as one of the amino acids in the dipeptide or tripeptide with the remaining amino acids consisting of isoleucine, leucine, valine, or in the case of a tripeptide, combinations thereof. Such prodrugs are converted into the individual amino acids in the bloodstream. Suitable dosages of progdugs would be 0.5-5 g per day. The prodrugs can be administered in the same manner as the amino acid preparations.

In addition to the branched chain amino acid formulations described above, the homocysteine lowering agent can be selected from odd-chain fatty acids, propionyl CoA, biotin (a co-factor for propionyl CoA carboxylase) and alpha-ketobutyrate, each alone or in combination with branched chain amino acids. These agents can be administered by any method, such as intradermal, intramuscular, intraperitoneal, intravenous, subcutaneous, intranasal, transdermal and oral routes. Suitable dosages of these agents would be from 0.5-5 g/day. In respect of these agents, it is known that the branched-chain amino acids and odd-chain fatty acids can be directly metabolized into propionyl CoA, which is subsequently converted into L-methylmalonyl CoA and then into succinyl CoA by the enzyme methylmalonyl CoA mutase (MCM). Succinyl CoA is then utilized in the electron transport chain for generation of cellular energy. Isoleucine, valine, and propionyl CoA upregulate the expression MCM message by 4-fold in brain astrocytes, in vitro (Narasimhan, et al. (1996). J Neurosci Vol. 16(22): 7336-46). Further, while not intending to be bound by any particular theory, it is considered that the isoleucine-induced upregulation of MCM enhances the metabolism of homocysteine into alpha-ketobutyrate, which is converted into propionyl CoA to then be used as a substrate for MCM. Accordingly, compounds that induce MCM, such as propionyl CoA or compounds metabolized into propionyl CoA may also be used to reduce homocysteine levels according to the invention.

The following Example is intended to illustrate the invention and is not meant to be limiting.

EXAMPLE 1

This Example demonstrates the lowering of the amount of serum homocysteine levels in a group of individuals by administration of L-isoleucine.

L-isoleucine therapy (3-5 grams/day divided into two doses per day) was administered to 17 postmenopausal women for 10 weeks. The L-isoleucine therapy was associated with an 11% average reduction in serum homocysteine levels among 14 post menopausal woman experiencing hot flashes. In 5 participants, there was a >20% reduction in serum homocysteine and 2 participants showed a >30% reduction. Only one of the 14 participants showed an increase in homocysteine associated with L-isoleucine therapy (Table 1).

There were no significant changes in serum folate or vitamin B12 levels associated with L-isoleucine therapy. The participant demonstrating the largest decrease in homocysteine had a slight decrease in folate and B12 associated with L-isoleucine therapy. None of the participants had clinically low folate or B12 at baseline or while on treatment.

TABLE 1

|  | homocysteine (umol/L) | % reduction | folate | B12 |
|---|---|---|---|---|
| 1f | 8.5 | 0.223529412 | 18.2 | 516 |
| 1l | 6.6 |  | 25 | 681 |
| 2f | 9.6 | 0.302083333 | 16.9 | 384 |
| 2l | 6.7 |  | 17.4 | 298 |
| 3f | 13.3 | 0.263157895 | 20.2 | 362 |
| 3l | 9.8 |  | 17 | 417 |
| 4f | 6.9 | 0.304347826 | 25 | 741 |
| 4l | 4.8 |  | 20.7 | 653 |
| 5f | 9.3 | 0.247311828 | 25 | 774 |
| 5l | 7 |  | 14.3 | 807 |
| 6f | 7.2 | 0.013888889 | 25 | 992 |
| 6l | 7.1 |  | 20.4 | 832 |
| 7f | 8.7 | 0 | 25 | 540 |
| 7l | 8.7 |  | 21.8 | 647 |
| 8f | 9.1 | 0.131868132 | 14 | 392 |
| 8l | 7.9 |  | 13 | 382 |
| 9f | 6.4 | 0.046875 | 8.5 | 705 |
| 9l | 6.1 |  | 20.3 | 820 |
| 10f | 7.1 | 0.014084507 | 21.9 | 1009 |

TABLE 1-continued

|  | homocysteine (umol/L) | % reduction | folate | B12 |
|---|---|---|---|---|
| 10l | 7 |  | 19.4 | 917 |
| 11f | 10.9 | 0.009174312 | 15.1 | 195 |
| 11l | 10.8 |  | 14.6 | 290 |
| 12f | 6.7 | −0.23880597 | 17.3 | 467 |
| 12l | 8.3 |  | 12.6 | 441 |
| 13f | 8.6 | 0.034883721 | 19.7 | 338 |
| 13l | 8.3 |  | 13.6 | 446 |
| 16f | 5.9 |  | 18.9 | 786 |
| 16l |  |  | 18.2 | 1065 |
| 17f | 6.2 | 0.177419355 | 18.2 | 424 |
| 17l | 5.1 |  | 19.6 | 543 | average reduction = 0.109272731
f= baseline values
l= 10 week values

Thus, this Example demonstrates that the amount of homocysteine in the blood of an individual can be reduced by administration of L-isoleucine.

While this invention has been illustrated by specific embodiments, routine modifications will be apparent to those skilled in the art and such modifications are intended to be within the scope of the invention and the following claims.

The invention claimed is:

1. A method for lowering the amount of homocysteine in the blood of an individual comprising administering to the individual in need thereof an amount of a composition comprising a homocysteine lowering agent effective to lower the amount of homocysteine in the blood of the individual, wherein the agent is selected from the group consisting of:
   a) dipeptides consisting of isoleucine, leucine, valine, or glycine, and combinations thereof;
   b) tripeptides consisting of isoleucine, leucine, valine, or glycine, and combinations thereof;
   c) alpha-ketobutyrate;
   d) propionyl CoA; and
   e) combinations of a) through d);
   wherein the amount of homocysteine in the blood of the individual after administration of the agent is lower in comparison to the amount of homocysteine in the blood of the individual prior to administration of the agent.

2. The method of claim 1, wherein the dipeptides or tripeptides of a) or b) comprise glycine and are administered in a dosage of from 0.5-5 grams per day.

3. The method of claim 1, wherein the agent is an L-isoleucine dipeptide.

4. The method of claim 1, wherein the agent is a dipeptide consisting of L-isoleucine and one of L-valine or L-leucine.

5. The method of claim 1, wherein the agent is an L-isoleucine tripeptide.

6. The method of claim 1, wherein the agent is a tripeptide consisting of at least one L-isoleucine and L-leucine or L-valine.

7. The method of claim 1, wherein the agent is a tripeptide consisting of L-isoleucine, L-leucine and L-valine.

8. The method of claim 1, wherein the composition is administered orally.

9. The method of claim 1, wherein the agent is selected from alpha-ketobutyrate and propionyl CoA.

* * * * *